United States Patent [19]

Arms

[11] Patent Number: 4,813,435
[45] Date of Patent: Mar. 21, 1989

[54] IMPLANTABLE DISPLACEMENT SENSOR MEANS

[75] Inventor: Steven W. Arms, Burlington, Vt.

[73] Assignee: Micro Strain Company, Burlington, Vt.

[21] Appl. No.: 185,918

[22] Filed: Apr. 25, 1988

[51] Int. Cl.⁴ .................................................. A61B 5/10
[52] U.S. Cl. ....................................... 128/774; 73/768
[58] Field of Search ........................ 310/338; 324/207; 128/774, 782; 73/779, 768, DIG. 3, DIG. 4

[56] References Cited

U.S. PATENT DOCUMENTS 4,204,544  5/1980  Feldstein et al. ................... 128/774

FOREIGN PATENT DOCUMENTS 134601  of 1986  Japan ................................... 324/207
1254319  8/1986  U.S.S.R. ................................ 73/778

Primary Examiner—Max Hindenburg
Assistant Examiner—Scott M. Getzow
Attorney, Agent, or Firm—Thomas N. Neiman

[57] ABSTRACT

This device is adapted for replacable implantation in soft body tissue for the measurement of the mechanical behavior of the soft tissues of the body. The device consists of an hall-effect strain transducer that detects the linear motion of a magnetic core. A barb force transducer uses a barbed probe that is inserted into the soft tissue. The barb force transducer has pressure sensors located within the body of the probe that detect the squeezing of the tissue fibers against the sides of the transducer. The combination of the hall-effect strain transducer and the barb force transducer allows the operator to simultaneously measure the strain and force on a specific soft tissue.

7 Claims, 1 Drawing Sheet

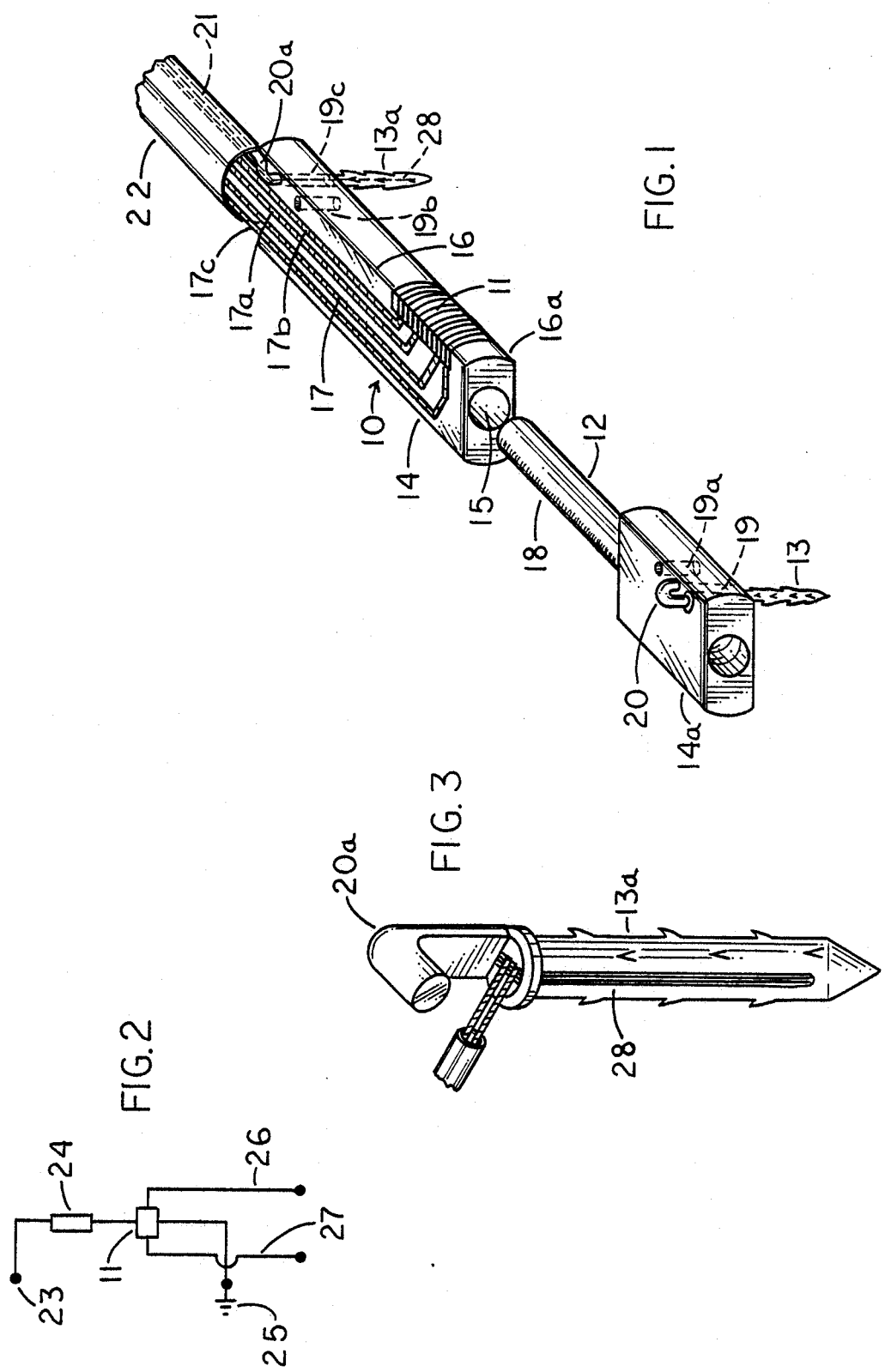

IMPLANTABLE DISPLACEMENT SENSOR MEANS

This invention pertains to biomedical measurement equipment and, in particular, to device which measures the force and strain in the soft tissue in the body simultaneously.

Many methods have been used to provide means for allowing individuals to measure movement or relative positioning of the parts of the body. The prior art includes a number of references which pertain to methods of detecting by electrical means the relative mechanical movement of parts of the body. The prior patents include a U.S. Pat. No. 4,294,015, issued to Gilbert Drouin on Oct. 13, 1981 for an Extensometer that shows a device that measures the deflection of a ligament from its normal range by means of a strain gage. The Patent issued to N. B. Nast et al, U.S. Pat. No. 2,605,635 for a Device for Measuring Small Longitudinal Changes uses a metalic substance and measures the change in inductance by means of voltage drop across the thin wire. The patent issued to Paul H. Brace, U.S. Pat. No. 4,319,236 on Mar. 9, 1982 for a Hall Effect Position Detector shows a device which measures the relative movement between two members, in this case between the coils of a spring, by the use of a Hall effect sensor. The disadvantages of this type device include the difficulty in adapting it for use in measuring the microscopic movements in the body and the need to be able to use it in limited, small areas of the body. As shown by the above-identified patents there is a real need felt by researchers to have a device that is simple to position and accurately align in order to allow proper measurement. Therefore, it is the object of this invention to teach a device that will provide means for accurately positioning and aligning a sensing device in position in soft tissue.

It is the another object of this invention to teach the use of a device that provides the flexibility necessary to be useful in a human body. Also, it is the object of this invention to teach a device that will provide the simultaneous measurement of the force and the strain that are being exerted by the soft tissue that is being measured at that particular time.

Finally, it is the object of this invention to teach an implantable displacement sensor means, for measuring the mechanical behavior of the soft tissues of the body, comprising a support base; said support base has a horizontal aperture located therein; electrical measuring means on said support base for determining linear motion; magnetic means; said magnetic means being located slidably within said horizontal aperture; said electrical means has transmission means attached; said support means has anchoring means; said support means has a plurality of vertical apertures; said anchoring means comprises at least one barbed extension; said extension has pressure sensing means inserted; and said pressure sensing means has information sending means.

Further objects of this invention, as well as the novel features thereof, will become more apparent by reference to the following description taken in conjunction with the following figures, in which:

FIG. 1 is a perspective view of the novel implantable dispacement sensor means;

FIG. 2 is a wiring diagram of the hall effect sensor; and

FIG. 3 is an enlarged side elevational view of the barbed probe showing the pressure sensor.

As shown in the figures, the implantable displacement sensor means 10 is comprised of a hall sensor 11 that is used to measure the displacement of a sliding magnetic core 12. Barbs 13 and 13a at each end of the sensor means 10 serve to position and anchor the device in the soft tissue. The magnetic core 12 is permanently attached to base 14a and may be slidably inserted into slot 15 located within base 14. The base has flat surfaces 16 and 16a on its top and bottom surfaces. This allows the hall sensor 11 and the bonding lead strips 17, 17a and 17b to be bonded to flat surfaces. The sliding magnetic core 12 has a permanent magnet 18 located within the core. Holes 19, 19a, 19b and 19c are drilled through the bases 14 and 14a and are designed to align the barbs and the base and also permit the insertion of an insertion tool. The insertion tool has two parallel projections which fit into holes 19a and 19b. This allows the assembly to be pushed into the tissue and, at the same time, allows control over the positioning of the unit. The alignment is designed to have the base 14 and the barbs 13 and 13a so that they are parallel to each other and perpendicular to the long axis of the base. The barbs 13 and 13a are formed with a loop 20 and 20a to keep the barb from being pulled through the base and allow the suture to be passed through the the loop to aid in the removal of the device from the body when its job is completed. The end 21 of barb 13a is extended to provide support for the flexible covering 22 that allows for protection and strain relief for the bonding lead strips 17, 17a and 17b.

The barb force transducer is located within the barb 13a and comprises pressure sensors 28. These sensors in the embodiment shown, comprise piezo electric materials, but can also be constructed of optical fibers or can be of strain gauge design. The output leads of the pressure sensor 28 are shown coming from barb 13a.

The wiring for the hall sensor is as follows. Positive supply voltage is provided through line 23. A constant current source 24 is used to excite the hall sensor 11. A ground 25 is connected to the sensor 11 and the output lines 26 and 27 are then brought to an instrumentation amplifier. The pressure sensing leads and the magnetic leads are covered by a silicone rubber coating or tubing 22 that provides bend relief at the exit of base 14.

The use of the above described device not only has research applications but may also have a large number of practical applications. The clinical potential include the optimizing of the surgical sucdess of tendon and ligament operations and for the mechanical integrity of healing tissues in order to optimize proper treatment during rehabilitation.

While I have described my invention in connection with a specific embodiment thereof, it is clearly understood that this is done only by way of example and not as a limitation to the scope of my invention as set forth in the objects thereof and in the appended claims.

I claim:

1. An implantable displaceable sensor means, for measuring the mechanical behavior of the soft tissue of the body, comprising:
   at least one support base;
   said support base has a horizontal aperture located therein;
   electrical measuring means on said support base for determining linear motion;
   magnetic means;

said magnetic means being located slidably within said horizontal aperture;

said electrical means has transmission means attached;

said support means has anchoring means;

said support means has a plurality of vertical apertures;

said anchoring means comprises at least one barbed extension;

said barbed extension has pressure sensing means located within said barbed extension; and said pressure sensing means has information sensing means.

2. An implantable displacement sensor means, according to claim 1, wherein:

said support base comprises two separate units; and said support base has flattened upper and lower surfaces.

3. An implantable displacement sensor means, according to claim 1, wherein:

said electrical measuring means comprises a hall-effect generator and said magnetic means.

4. An implantable displacement sensor means, according to claim 1, wherein:

said magnetic means comprises a sliding core to which a magnet is attached; and said sliding core is connected to one part of said support base and inserted into said horizontal aperture of the other side of said support base.

5. An implantable displacement sensor means, according to claim 1, wherein:

said transmission means has protection means; and said protection means comprises flexible tubing.

6. An implantable displacement sensor means, according to claim 1, wherein:

said barbed extension has hook means located on the end opposite the barbed end of said extension for maintaining pressure on said support base and for providing tieing means for a suture.

7. An implantable displacement sensor means, according to claim 1, wherein:

said barbed extension has a hollowed center section for permitting insertion of said pressure sensing means; and said pressure sensing means comprises piezo electric materials.

* * * * *